United States Patent [19]

Beyerle et al.

[11] Patent Number: 5,455,050
[45] Date of Patent: Oct. 3, 1995

[54] AQUEOUS ANTACIDS WITH CALCIUM CARBONATE AND MAGNESIUM SALT

[75] Inventors: Douglas S. Beyerle, Horsham; Gerard P. McNally, Strafford, both of Pa.

[73] Assignee: McNeil-PPC, Inc., Milltown, N.J.

[21] Appl. No.: 153,005

[22] Filed: Nov. 12, 1993

[51] Int. Cl.$^6$ .......................... A61K 33/06; A61K 33/08; A61K 33/10; A61K 33/12
[52] U.S. Cl. .......................... 424/682; 424/683; 424/684; 424/685; 424/686; 424/687; 424/6833304691; 424/692; 514/782
[58] Field of Search ...................... 514/782; 424/682–692

[56] References Cited

U.S. PATENT DOCUMENTS

| | | | |
|---|---|---|---|
| 3,621,094 | 11/1971 | Mayron et al. | 424/128 |
| 4,468,381 | 8/1984 | Mitra et al. | 424/158 |
| 4,744,986 | 5/1988 | Luber et al. | 424/156 |
| 4,869,902 | 9/1989 | Buehler et al. | 424/686 |
| 5,112,813 | 5/1992 | Luber et al. | 514/54 |
| 5,140,760 | 8/1992 | Withington | 424/81 |
| 5,272,137 | 12/1993 | Blase et al. | 514/54 |
| 5,296,241 | 3/1994 | Brimberg et al. | 424/682 |

FOREIGN PATENT DOCUMENTS

| | | |
|---|---|---|
| 2512344 | 3/1983 | France . |
| 60-161915 | 8/1985 | Japan . |

OTHER PUBLICATIONS

PDR for Nonprescription Drugs, 14th Ed., pp. 566–567 (1993).
Product Label from MARBLEN Antacid, Fleming & Co. (Lot No. 0028788, Expiration Date Feb. 1995).

*Primary Examiner*—Shep K. Rose
*Attorney, Agent, or Firm*—Bernard F. Plantz

[57] ABSTRACT

The present invention relates to an aqueous pharmaceutical suspension for oral use, and a method of preparation, having antacid and antiulcer properties which contains a therapeutically effective amount of calcium carbonate in combination with magnesium carbonate and/or magnesium trisilicate and a carboxylic acid pH adjusting agent.

14 Claims, No Drawings

AQUEOUS ANTACIDS WITH CALCIUM CARBONATE AND MAGNESIUM SALT

FIELD OF THE INVENTION

This invention relates to new pharmaceutically elegant antacid compositions and their method of preparation. More specifically, this invention relates to aqueous pharmaceutical suspensions for oral use having antacid and antiulcer properties which contain a therapeutically effective amount of calcium carbonate in combination with magnesium carbonate and/or magnesium trisilicate as the sole active antacid component.

BACKGROUND OF THE INVENTION

Calcium carbonate, magnesium carbonate and magnesium trisilicate are known gastric antacids (for example, see *Remington's Pharmaceutical Sciences*, 18th Edtn., 1990, published by Mack Publishing Co., Chapter 39 on "Gastrointestinal Drugs) with relatively fast onset of action and prolonged duration of action. However, as noted on page 779 of the Remington reference, which provides a tabular listing of twenty-six proprietary antacid suspensions, only one indicates a combination of calcium carbonate with a magnesium salt (magnesium carbonate) for the product Marblen (Fleming).

It has been observed that aqueous antacid suspensions of calcium carbonate in combination with magnesium carbonate and/or magnesium trisilicate yield very alkaline compositions with a pH of about 9 or even higher to about 9.9. Such high alkalinity is disadvantageous for commercial purposes, for example, preservatives in the formulation such as parabens will break down and lose efficacy over time at such high pH's.

SUMMARY OF THE INVENTION

The present invention thus provides aqueous antacid suspensions with a lower pH of about 7.5–8.5, and preferably about 8.0–8.3, with as the antacid component the commercially seldom used calcium carbonate, magnesium carbonate and/or magnesium trisilicate antacids. In addition to a commercially acceptable pH range, the suspensions of this invention are stable with regard to viscosity, defoaming, sedimentation and acid neutralizing capacity (ANC) parameters and redisperse well upon shaking. As described hereinafter, it is the selective order of mixing the essential components of the present invention which provides the desirably lower pH.

DETAILED DESCRIPTION OF THE PREFERRED EMBODIMENTS

The aqueous suspensions of the present invention contain an effective antacid amount of calcium carbonate in combination with a magnesium salt selected from the group consisting of magnesium carbonate, magnesium trisilicate and mixtures thereof. This calcium carbonate/magnesium salt combinate is the sole active antacid component in the suspension. The suspension contains from about 1.5 to about 20, preferably about 5 to about 15, percent weight/volume of the calcium carbonate and from about 1.0 to about 20, preferably about 2 to about 8, percent weight/volume of the magnesium salt, based on the volume of the aqueous antacid suspension.

The calcium carbonate, magnesium carbonate and magnesium trisilicate active ingredients are utilized in the present invention as individual powders rather than in gel or paste form. Micronized powders are found to be most suitable, preferably with 100% particle size distribution of about 0.1–20, and preferably about 0.1–10 microns. Such small particle size has a tremendous advantageous effect on the sedimentation rate of the suspension and, more importantly, it helps achieve optimal mouthfeel to the user.

The present invention also makes use of an effective suspending amount of a suitable thickening agent generally used in aqueous antacid formulations, for example, xanthan gum (preferred), guar gum, methyl celluloses such as hydroxypropyl methyl cellulose (HPMC) and sodium carboxymethylcellulose, and the like. Since the active antacids are utilized in powder form instead of gels or pastes, which tend to contribute more to the final viscosity, the thickening agent component needs to provide a substantial viscosity to the finished product. For purposes of this invention, the particular thickening agent(s) employed, and the amount thereof, should be such so as to provide a viscosity range in the final product of from about 1000 centipoise (cps) to about 3000 cps, as determined on a Brookfield LVT viscometer (25° C., spindle no. 2, rotation speed 12 for 3 minutes). In general, from about 0.1 to about 1.0 percent weight/volume of the thickening agent, based on the volume of final product, has been found suitable.

An appropriate liquid wetting agent such as glycerin may be utilized to insure maximum dispersion of the thickening agent in the aqueous system. From about 0.5 to about 20.0, and preferably from about 2.0 to about 7.5 weight/volume percent of glycerin has been found suitable. The thickening agent is dispersed in the glycerin in a separate container with thorough mixing prior to its utilization. An alternative to the thickening agent/glycerin premix is the use of appropriate mechanical dispersing means such as a high shear mixer to assist dispersion of the thickening agent. A further alternative is to use one of the readily dispersible thickening agents commercially available, for example, the KELTROL RD brand of readily dispersed xanthan gum from Kelco, division of Merck. Such readily dispersible thickening agents provide adequate dispersion upon direct addition to the aqueous system. The need for premixing with a wetting agent is thus eliminated although premixing may still be utilized.

As noted previously, the high pH levels inherent in the use of magnesium carbonate and/or magnesium trisilicate, about 9 or higher, are deemed too high to achieve and maintain an efficient preservative system. Accordingly, a carboxylic acid pH adjusting agent is included as an essential component of the present invention. Tartaric acid has been found to be the preferred pH adjusting agent, although other carboxylic acids such as adipic, benzoic, carbonic, cinnamic, citric, fumaric, glutaric, gluconic, hydroxybenzoic, malonic, malic, phthalic, oxalic, sorbic, succinic and the like may be utilized. The amount of the carboxylic acid pH adjusting agent should be sufficient to bring and maintain the pH of the final product in a range of about 7.5–8.5 and preferably about 8.0–8.3. In general from about 0.2 to about 2.0 weight/volume percent of the pH adjusting agent has been found suitable. For example, with about 0.5 weight/volume percent of tartaric acid, a stable pH of about 8.2 has been maintained at one year.

Any desired pharmaceutically acceptable adjuvant used in liquid antacid preparations by those skilled in the art may also be employed. For example, one or more preservatives such as methylparaben, butylparaben or propylparaben, and sweetening and/or flavoring agents such as oil of orange, imitation wintergreen flavor, lemon-lime flavors, mint flavors, or combinations thereof, are commonly utilized. Sorbitol serves to increase shelf life and palatability. Further, other actives such as antispasmodic agents, tranquilizers or other medicaments can be optionally included. Simethicone, for example, which is not an antacid, is an antiflatuent frequently used in antacid compositions to defoam gastric juice in order to decrease the incidence of gastroesophageal reflux. In general, an effective antiflatuent amount is employed, and from about 0.1 to about 2.0 weight/volume percent is found suitable.

A unique aspect of the present invention is the order in which the essential components are mixed in order to achieve this desired pH range of about 7.5–8.5, and preferably about 8.0–8.3. If the pH adjusting agent is added to the active antacids prior to the thickening agent, it tends to react with the active antacids and the result is a higher pH (>9). It is critical, therefore, that the thickening agent be added to the aqueous dispersion of the particulate antacids with thorough admixture prior to addition of the pH adjusting agent. The thickening agent is stirred for a time sufficient to substantially coat the particulate antacids such that the grittiness perceived from the powdered materials is negligible and, more importantly, the protective coating prevents unwanted reaction between the carboxylic acid pH adjusting agent and the active antacids and the result is a lower pH.

In the event that other additives or active medicaments are to be included which are likewise susceptible to reaction or degradation with the carboxylic acid pH adjusting agent, for example, simethicone, then these should be either similarly precoated with the thickening agent or utilized in the form of a compatible liquid. Preferably the simethicone is in the form of an aqueous dispersion or emulsion. These dispersions and emulsions are commercially available, and generally contain about 30–50 weight/volume percent of simethicone, based on the volume of the aqueous dispersion or emulsion.

The present invention thus provides a method of preparing a stable aqueous antacid suspension for oral use with a pH about 7.5–8.5 of calcium carbonate in combination with a magnesium salt consisting of magnesium carbonate, magnesium trisilicate or a mixture thereof, which comprises in the order specified the steps of:

(a) adding to water an effective antacid amount of particulate calcium carbonate and said magnesium salt, each in the form of a micronized powder with 100% particle size distribution of about 0.1–20, preferably about 0.1–10, microns with mixing until the particulate material is completely wetted and dispersed;

(b) adding to said dispersion with stirring from about 0.1 to about 1.0 weight/volume percent of a thickening agent for a time sufficient to substantially coat said particulate material and to produce a suspension;

(c) adding to said suspension with stirring an effective amount of a carboxylic acid pH adjusting agent to provide a pH of about 7.5–8.5 to the final aqueous antacid suspension; and (d) optionally adding with stirring at least one pharmaceutically acceptable adjuvant or at any of steps (a), (b) or (c).

If deemed necessary, the following additional steps may be performed:

(e) adding to said suspension water to bring the volume to 100; and (f) stirring to obtain uniform suspension.

When sorbitol or flavorants or sweeteners or preservatives are added, they may be added to any one of steps (a) to (d).

Prior to packaging, the suspension is sterilized by pasteurization or by chemicals such as sodium hypochlorite or hydrogen peroxide.

The invention will be made clearer in the examples which follow. All percentages are weight/volume (grams/liter). These examples are given by way of illustration and are not to be taken as limiting.

EXAMPLE I

The following compositions illustrate the present invention.

|  | Percent W/V | |
| --- | --- | --- |
| Ingredients | A | B |
| Deionized Water | 53.6–66.04 | 53.6–66.04 |
| Sorbitol | 5.0–30.0 | 10.0–20.0 |
| Glycerin | 0.5–20.0 | 2.0–7.5 |
| Xanthan Gum (KELTROL RD) | 0.1–1.0 | 0.25–0.75 |
| Simethicone[a] | 0.5–10.0 | 1.0–3.0 |
| Calcium Carbonate[b] | 1.5–20.0 | 5.0–15.0 |
| Magnesium Carbonate[c,d] | 1.0–20.0 | 2.0–8.0 |
| Tartaric Acid | 0.2–2.0 | 0.35–0.65 |
| Butylparaben | 0.02 | 0.02 |
| Propylparaben | 0.03 | 0.03 |
| Flavorants (liquid) | 0.3–1.0 | 0.3–1.0 |
| Water Q.S. | 100 | 100 |
| pH | 7.6–8.5 | 8.0–8.4 |

[a]30% aqueous emulsion or dispersion
[b]Average particle size 100% distribution <10 microns.
[c]Average particle size 100% distribution <10 microns.
[d]Alternatively magnesium trisilicate.

In a suitable preparation vessel, add the sorbitol to the water and mix for ten minutes. Add the simethicone and mix for ten minutes. Add the calcium carbonate and mix for fifteen minutes. Add the magnesium carbonate and mix for fifteen minutes. In a separate vessel, add the xanthan gum to the glycerin and mix for fifteen minutes and then add mixture to the preparation vessel with mixing for twenty minutes. Add the tartaric acid and mix for twenty minutes. In a separate vessel add the parabens and flavorants and mix until parabens are dissolved and then add mixture to the preparation vessel with mixing for thirty minutes. If necessary, add water to bring volume to 100 and continue stirring to obtain uniform suspension. The suspension is then pasteurized at 70° C. for 2–60 minutes.

EXAMPLE II

The following suspension were prepared using the procedure described in Example I. The suspension was sterilized by pasteurization at 70° C. for 2 minutes.

|  | Percent W/V | |
| --- | --- | --- |
| Ingredients | A | B |
| Deionized Water | 66.04 | 53.6 |
| Sorbitol | 15.0 | 15.0 |
| Glycerin | 5.0 | 5.0 |
| Xanthan Gum (KELTROL RD) | 0.60 | 0.6 |
| Simethicone[a] | 1.4 | 2.8 |
| Calcium Carbonate[b] | 8.0 | 16.0 |
| Magnesium Carbonate[c] | 3.0 | 6.0 |
| Tartaric Acid | 0.5 | 0.5 |
| Butylparaben | 0.02 | 0.02 |

-continued

| Ingredients | Percent W/V | |
| --- | --- | --- |
| | A | B |
| Propylparaben | 0.03 | 0.03 |
| Flavorants (liquid) | 0.03–1.0 | 0.3–1.0 |
| Water Q.S. | 100 | 100 |
| pH | 8.2 | 8.2 |

[a]30% aqueous emulsion or dispersion
[b]Average particle size 100% distribution <10 microns.
[c]Average particle size 100% distribution <10 microns.

EXAMPLE III

The following suspension was prepared using the procedure of Example I, except the sequence of ingredient addition was modified as shown below. The suspension was not sterilized because of the unacceptable pH.

| Ingredients | Percent W/V |
| --- | --- |
| Soribtol | 15.0 |
| Xanthan Gum (KELTROL T) | 0.3 |
| Simethicone[a] | 2.7 |
| Calcium Carbonate[b] | 16.2 |
| Magnesium Carbonate[c] | 5.8 |
| Tartaric Acid | 0.5 |
| Butylparaben | 0.02 |
| Propylparaben | 0.03 |
| Flavors/Saccharin | 0.66 |
| Deionized Water Q.S. | 100 |
| pH | 8.85 |

[a]30% aqueous emulsion or dispersion
[b]Average particle size 100% distribution <10 microns.
[c]Average particle size 100% distribution <10 microns.

Sequence of ingredient addition to vessel:

(a) Add sorbitol and water;

(b) Add simethicone;

(c) Add tartaric acid;

(d) Add xanthan gum;

(e) Add calcium carbonate and magnesium carbonate;

(f) Dissolve parabens/saccharin in flavors and add to vessel; and (g) Q.S. to 1000 ml of water.

When the antacids were added in step (e), the calcium carbonate reacted (foamed) with the tartaric acid because the antacid powders were not adequately coated with the xanthan gum. This example illustrates the importance of mixing the xanthan gum and the antacid so that the antacid particles are adequately coated with the gum before the tartic acid is added to the vessel.

Various modifications can be made to the above-described embodiments without departing from the spirit and scope of the present invention.

What is claimed is:

1. A method of preparing a stable aqueous antacid suspension for oral use having a pH of about 7.5 to about 8.5 of calcium carbonate in combination with a magnesium salt selected from the group consisting of magnesium carbonate, magnesium trisilicate and a mixture thereof as the sole active antacid component, which comprises in the order specified the steps of:

(a) adding to water an effective antacid amount of particulate calcium carbonate and said magnesium salt, each in the particulate form of a micronized powder with 100% particle size distribution of about 0.1 to about 20 microns with mixing until the particulate material is completely wetted and dispersed;

(b) adding to said dispersion with stirring an effective suspending amount of a thickening agent for a time sufficient to substantially coat said particulate material and to produce a suspension; and (c) adding to said suspension with stirring an effective pH adjusting amount of a carboxylic acid pH adjusting agent to provide a pH of about 7.5 to about 8.5 to the aqueous antacid suspension.

2. The method of claim 1 wherein said antacid amount of calcium carbonate is from about 1.5 to about 20.0 percent weight/volume and of the magnesium salt is from about 1.0 to about 20.0 percent weight/volume, based on the volume of the aqueous antacid suspension.

3. The method of claim 1 wherein said pH is about 8.0 to about 8.3.

4. The method of claim 1 wherein said thickening agent in step (b) is xanthan gum.

5. The method of claim 1 wherein said thickening agent is step (b) is xanthan gum premixed with glycerin.

6. The method of claim 1 wherein said pH adjusting agent in step (c) is tartaric acid.

7. The method of claim 1 further comprising (d) adding with stirring at least one pharmaceutically acceptable adjuvant or at any of steps (a), (b) or (c).

8. The method of claim 7 wherein said adjuvant in step (d) is an effective antiflatuent amount of simethicone.

9. The method of claim 7 wherein said adjuvant in step (d) is an effective antiflatuent amount of simethicone, one or more preservatives, sorbitol and one or more flavorants.

10. The method of claim 1 wherein the amount of said thickening agent is from about 0.1 to about 1.0 percent weight/volume, based on the volume of the aqueous antacid suspension.

11. The method of claim 1 wherein said particle size distribution is about 0.1 to about 10 microns.

12. A method of preparing a stable aqueous antacid suspension for oral use with pH of about 8.0 to about 8.3 of calcium carbonate and magnesium carbonate as the sole active antacid component, which comprises in the order specified the steps of:

(a) adding to water an effective antacid amount of particulate calcium carbonate and particulate magnesium carbonate, each in the form of a micronized powder with 100% particle size distribution of about 0.1 to about 20 microns with mixing until the particulate material is completely wetted and dispersed;

(b) adding to said dispersion an effective suspending amount of xanthan gum or xanthan gum premixed with glycerin, with stirring for a time sufficient to substantially coat said particulate material and to provide a suspension; and (c) adding to said suspension with stirring an effective pH adjusting amount of tartaric acid to provide a pH of about 8.0 to about 8.3 to the final antacid suspension.

13. The method of claim 12 further comprising (d) adding with stirring at least one pharmaceutically acceptable adjuvant or at any of steps (a), (b) or (c).

14. The method of claim 12 wherein said particle size distribution is about 0.1 to about 10 microns.

* * * * *